US00PP15976P2

(12) United States Plant Patent
Mowrey et al.

(10) Patent No.: US PP15,976 P2
(45) Date of Patent: Sep. 20, 2005

(54) PLUM TREE NAMED 'SUPLUMTWENTYSIX'

(50) Latin Name: *Prunus salicina*
Varietal Denomination: Suplumtwentysix

(75) Inventors: Bruce D. Mowrey, Watsonville, CA (US); David W. Cain, Bakersfield, CA (US); Carlos D. Fear, Aptos, CA (US)

(73) Assignee: Sun World International, Inc., Bakersfield, CA (US)

( * ) Notice: Subject to any disclaimer, the term of this patent is extended or adjusted under 35 U.S.C. 154(b) by 45 days.

(21) Appl. No.: 10/867,891

(22) Filed: Jun. 14, 2004

(51) Int. Cl.[7] ..... A01H 5/00
(52) U.S. Cl. ..... Plt./184
(58) Field of Search ..... Plt./184

*Primary Examiner*—Anne Marie Grunberg
*Assistant Examiner*—June Hwu
(74) *Attorney, Agent, or Firm*—Knobbe, Martens, Olson & Bear, LLP

(57) ABSTRACT

A new and distinct plum tree variety, *Prunus salicina,* 'Suplumtwentysix' characterized by consistent heavy production of large (61 mm), reddish-black plums with amber-colored flesh, which ripen in late May to early June in Kern County. The eating quality of plums produced by 'Suplumtwentysix' is relatively good for the early season, with juicy sweet-tart flesh and mildly tart skin.

1 Drawing Sheet

Latin name of the genus and species claimed: *Prunus salicina.*

Variety denomination: 'Suplumtwentysix'.

BACKGROUND OF THE INVENTION

The present invention relates to a new and distinct variety of plum tree, herein after referred to by the cultivar name 'Suplumtwentysix'. The new variety 'Suplumtwentysix' originated by hybridization, being first hybridized by Carlos Fear in Kern County, Calif., and was selected by Bruce Mowrey. The new variety was first evaluated by Bruce Mowrey and David Cain near Wasco, Calif. in Kern County.

SUMMARY OF THE INVENTION

'Suplumtwentysix' is characterized by consistent heavy production of large (approximately 61 mm), reddish-black plums with a round to slightly flatttened shape, and amber colored flesh. The fruit ripens in late May to early June in Kern County, Calif. The plums have an eating quality that is relatively good for the early season, with juicy sweet-tart flesh that has approximately 15° brix. The skin is medium-thin and mildly tart.

The seed parent of the new variety 'Suplumtwentysix' is the plum tree variety 'Ambra' (unpatented). The pollen parent is '438-432' (unpatented), that was selected from a progeny of the plum tree variety 'Queen Rosa' (unpatented) crossed with pollen of the plum tree variety 'Black Beaut' (unpatented). The parent varieties were first crossed in 1990, with the date of planting of February 1991, and the date of first flowering being March 1992. The new variety 'Suplumtwentysix' was first selected by Bruce Mowrey as '93P-003' in 1993. The new plum variety was first asexually propagated by Bruce Mowrey near Wasco, Kern County, Calif. in 1994, by budding onto 'Nemared' (unpatented) rootstock.

The new variety 'Suplumtwentysix' resembles its seed parent, 'Ambra' in that they both have amber flesh and reddish-black skin. The new variety can be distinguished from 'Ambra' in that 'Suplumtwentysix' ripens approximately seven days earlier than 'Ambra' and has larger-sized fruit than 'Ambra' (approximately 61 mm diameter for 'Suplumtwentysix' versus approximately 58 mm diameter for 'Ambra').

The new variety 'Suplumtwentysix' resembles its pollen parent, '438-432' in that both of the varieties ripen at approximately the same time. The new variety may be distinguished from '438-432' by possessing larger-sized fruit and skin that is reddish-black compared to the red skin of the pollen parent '438-432.'

The new plum variety 'Suplumtwentysix' may be distinguished from presently available cultivars in commerce by the following combination of characteristics: the new variety most nearly resembles the variety 'Black Beaut' (unpatented). It may be distinguished from 'Black Beaut' in that it ripens approximately 16 days earlier and possesses a more productive and consistent yield than 'Black Beaut'.

The new variety 'Suplumtwentysix' has been shown to maintain its distinguishing characteristics through successive asexual propagation by, for example, budding onto 'Nemared' (unpatented) rootstock.

BRIEF DESCRIPTION OF THE FIGURE

The accompanying color photographic illustration (FIG. 1) shows typical specimens of the foliage and fruit of the new plum tree variety 'Suplumtwentysix.' The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The new variety 'Suplumtwentysix' has not been observed under all possible environmental conditions. The phenotype may vary somewhat with variations in environment such as temperature, daylength, and light intensity, without, however, any variance in genotype.

The descriptive matter which follows pertains to 8 year old 'Suplumtwentysix' plants grown in the vicinity of Wasco, Kern County, Calif., during 2002, and is believed to apply to plants of the variety grown under similar conditions of soil and climate elsewhere.

TREE

General: (measurements taken on 8 year old tree unless otherwise noted).

*Tree size.*—Medium. Normal for most plum varieties. Reaches a height of approximately 3.5 meters with normal pruning.

*Tree vigor.*—Vigorous; growth of approximately 1.8 to approximately 2 meters height the first growing season.

*Tree growth.*—Upright-spreading.

*Tree productivity.*—Productive. Fruit set is usually two or more times desired amount for marketable size fruit. Thinning and spacing of fruit is necessary.

*Tree form.*—Vase formed.

*Bearer.*—Regular. No alternate bearing observed.

*Fertility.*—Self-sterile, pollinizer required.

*Tree canopy density.*—Dense. Pruning is required to open tree vase shape, allowing more sunlight to center of tree.

*Tree hardiness.*—Hardy in all fruit growing areas of California. Winter chilling requirement is approximately 650 hours at or below 7.2° C.

*Tree disease resistance/susceptibility.*—No specific testing for relative plant disease resistance/susceptibility has been designed. Under close observation in Wasco, Kern County, Calif., no particular plant/fruit disease resistance/susceptibility has been observed.

Trunk (measurements at approximately 30 cm above soil line).

*Trunk diameter.*—Approximately 20 cm. Varies with soil type, fertility, climatic conditions and cultural practices.

*Trunk texture.*—Medium shaggy, increases with age of tree.

*Trunk color.*—Near Greyed-green 196B to Greyed-green 197A on exposed areas, and near Greyed-orange 164B in recesses. Becomes darker with age.

Branches: (measurements at approximately 90 cm above soil line).

*Branch size.*—Diameter ranged from approximately 8 to approximately 11 cm.

*Branch texture.*—Smooth on 1$^{st}$ year wood, increasing roughness with tree age.

*Branch color.*—Branches vary from near Greyed-green 196B to Greyed-green 197A on exposed areas, and near Greyed-orange 164B in recesses. Becomes darker with age.

*Branch lenticels.*—Absent.

Flowering shoots: (data taken in July at midpoint of current-season growth).

*Flowering shoot size.*—Average diameter: approximately 5 mm.

*Flowering shoot color.*—Topside: Near Grey-brown 199A with slight green background.

*Underside: Near Grey-brown* 199A with slight green background.

*Flowering shoot lenticels.*—Plentiful — varies from approximately 10 to approximately 28 per linear centimeter. Lenticel number varies widely depending on environmental conditions and vigor of the plant.

*Flowering shoot leaf buds.*—Shape: Ovoid. Width: Approximately 1 mm. Length: Approximately 2 mm. Color: Near Greyed-orange 165A.

*Flowering shoot flower buds.*—Shape: Ovoid. Width: Approximately 2 mm. Color: Near Greyed-orange 165A. Number: Approximately 2 to 4.

LEAVES (data taken in July on fully expanded leaf at midpoint of current-season growth).

*Leaf size.*—Average length: Approximately 110 mm.

*Average width: Approximately* 45 mm.

*Leaf thickness.*—Medium.

*Leaf color.*—Upper surface: Near Green 137A. Lower surface: Near Green 137C.

*Leaf form.*—Elliptic.

*Tip.*—Acuminate.

*Base.*—Cuneate.

*Leaf margin.*—Moderately crenate.

*Leaf venation.*—Pinately net veined.

*Leaf surface texture.*—Smooth.

*Leaf petiole.*—Average length: Approximately 20 mm. Average diameter: Approximately 2 mm. Color: Near Green 138C.

*Leaf stipules.*—Number: 2 per leaf bud when present. Typical length: Approximately 3 to approximately 5 mm.

*Leaf glands.*—Form: Globose. Number: Varies from 3 to 6. Position: Alternate on upper portion of petiole and base of leaf blade. Average size: Approximately 0.4 mm by approximately 0.4 mm. Color: Near Greyed-orange 165A.

FLOWERS (fully opened)

General:

*Flower blooming period.*—First bloom: Feb. 26, 2002. Full bloom: Mar. 1, 2002.

*Flower size.*—Average diameter. Approximately 26 mm.

*Flower aroma.*—None.

Flower peduncle:

*Length.*—Approximately 9 mm.

*Diameter.*—Approximately 1 mm.

*Color.*—Near Green 142A.

Flower petals:

*Number.*—5.

*Arrangement.*—Slightly overlapping.

*Length.*—Approximately 11 mm.

*Diameter.*—Approximately 9 mm.

*Shape.*—Circular.

*Apex shape.*—Rounded.

*Base shape.*—Narrows at point of attachment.

*Color.*—White, with highlights of near Red 56D.

*Surface texture.*—Smooth.

*Margins.*—Smooth.

Flower sepals:
*Number.*—5.
*Length.*—Approximately 4.5 mm.
*Diameter.*—Approximately 2.5 mm.
*Shape.*—Obovate.
*Color.*—Near Green 142B.
*Surface texture.*—Smooth.

Flower stamens:
*Number.*—Approximately 24 to approximately 29, average 26.
*Average length.*—Approximately 7 mm.
*Filament color.*—White.
*Anther color.*—Near Greyed-yellow 160B, with highlights of near Red 39A.
*Pollen color.*—Near Greyed-yellow 160B with highlights of near Red 39A.

Flower pistil:
*Number.*—Usually one, occasionally two.
*Average length.*—Approximately 9 mm.
*Ovary diameter.*—Approximately 1 mm.
*Stigma position.*—Stigma extends slightly below anthers.

FRUIT

General: (data taken at firm-ripe on mature tree managed to obtain maximum quality).
*Fruit harvest.*—Date of first pick: Approximately May 23, 2002. Date of last pick: Approximately Jun. 2, 2002.

Fruit size:
*Length* (*stem end to apex*).—Approximately 51 mm.
*Diameter in line with suture plane.*—Approximately 61 mm.
*Diameter perpendicular to suture plane.*—Approximately 61 mm.
*Average weight.*—Approximately 115 gm.

Fruit form:
*Viewed from apex.*—Nearly round.
*Viewed from side, facing suture.*—Round-to-slightly flattened.
*Viewed from side, perpendicular to suture.*—Round-to-slightly flattened, slightly asymmetrical.

Fruit apex shape: Round-to-slightly flattened.

Fruit stem-end cavity depth: Shallow.

Fruit stem:
*Length.*—Approximately 7 mm.
*Diameter.*—Approximately 2 mm.
*Color.*—Near Green 143C.

Fruit skin:
*Thickness.*—Medium-to-thin.
*Adherence to flesh.*—Tenacious
*Surface texture.*—Slightly corrugated.
*Pubescence.*—None.
*Bloom.*—Moderate amount.
*Ground color.*—Near Yellow-green 145C when present.
*Overcolor.*—Reddish-black (near Greyed-purple 187B) when mature.
*Taste.*—Mildly tart.

Fruit flesh:
*Ripens.*—Slightly earlier on apex end.
*Texture.*—Fine, juicy, slightly soft.
*Fibers.*—Few, short.
*Flavor.*—Tart-sweet.
*Brix.*—Approximately 15 degrees.
*Juice.*—Plentiful.
*Aroma.*—Noticeable-to-strong.
*Color.*—Amber, (near Yellow-orange 23C) with slight greenish tint. Some red (near 42C) develops from the apex end as the fruit ripens.
*Pit cavity color.*—Near Yellow-Orange 23C.
*Pit cavity length.*—Approximately 20 mm.
*Pit cavity diameter in line with suture plane.*—Approximately 19 mm.
*Pit cavity diameter perpendicular to suture plane.*—Approximately 7 mm.

Fruit use: Dessert. Market, local and long distance.

Fruit shipping/keeping quality: Good. Holds well in cold storage for four weeks and maintains good firmness and eating quality. Minimal bruising and scarring in packing and shipping trials.

Stone: (measurements taken on dried stones).
*Stone freeness.*—Clingstone.
*Stone size.*—Length: Approximately 20 mm. Diameter in line with suture plane: Approximately 19 mm. Diameter perpendicular to suture plane: Approximately 7 mm.
*Stone form* (*viewed from side*).—Rounded.
*Stone form* (*viewed from stem side*).—Oval, symmetrical.
*Stone base shape.*—Rounded, retuse at stem attachment.
*Stone apex shape.*—Rounded with a small, sharp point.
*Stone surface.*—Irregularly furrowed near base. Lightly ridged toward base. Lightly pitted throughout.
*Stone halves.*—Nearly equal.
*Stone ridges.*—One ridge present on each side of the suture. The ridge is small and narrow beginning at the base and extending throughout the length of the stone.
*Stone outgrowing keel.*—Well developed.
*Stone tendency to split.*—Slight.
*Stone color.*—Near Greyed-orange 165B when dried.

What is claimed is:

1. A new and distinct variety of plum tree named 'Suplumtwentysix' as herein illustrated and described.

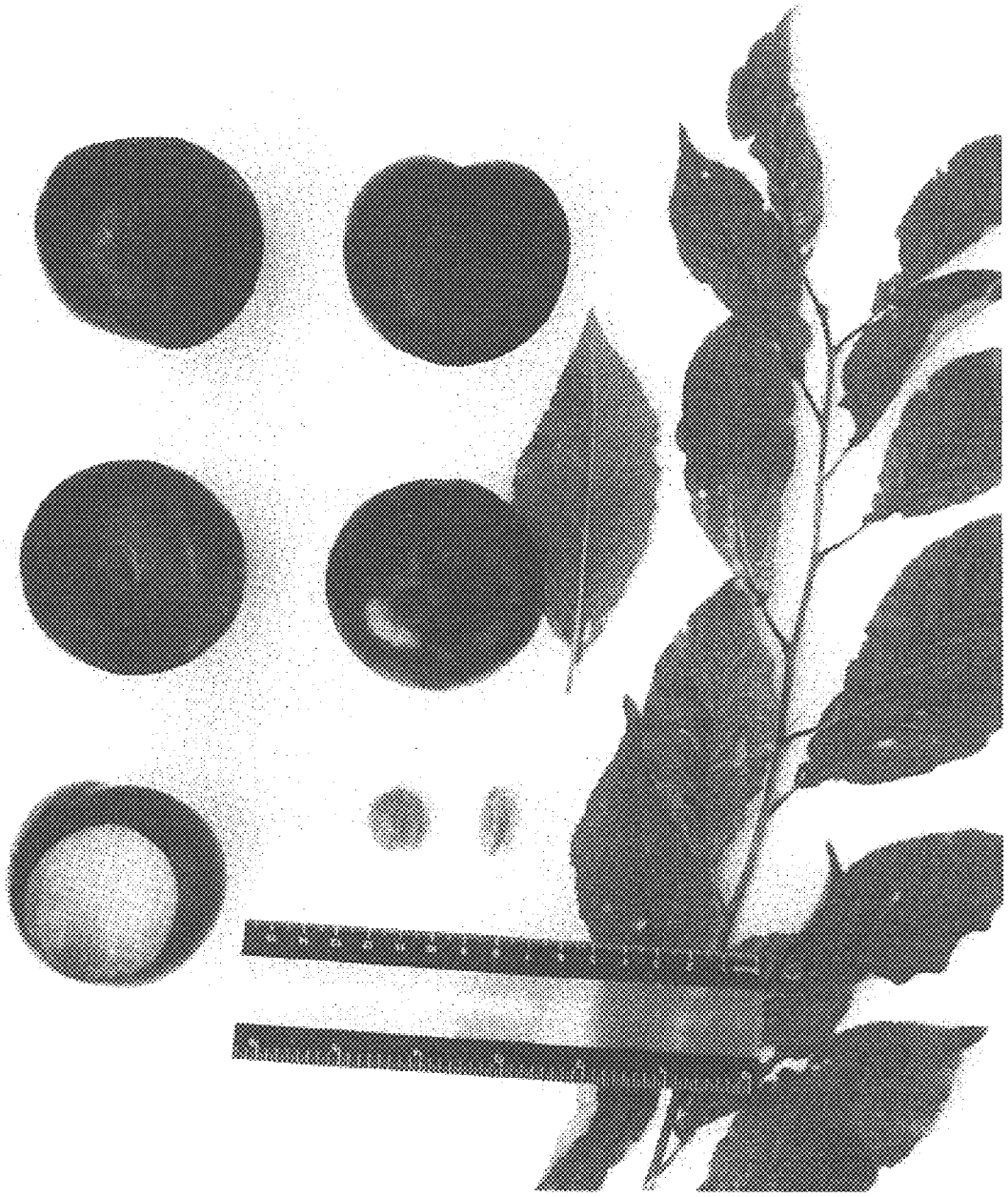

* * * * *